(12) United States Patent
Kopp

(10) Patent No.: US 8,640,705 B2
(45) Date of Patent: Feb. 4, 2014

(54) ANTI-SNORING DEVICE

(75) Inventor: Hans-Peter Kopp, Pfalzgrafenweiler (DE)

(73) Assignee: Erkodent Erich Kopp GmbH, Pfalzgrafenweiler (DE)

( * ) Notice: Subject to any disclaimer, the term of this patent is extended or adjusted under 35 U.S.C. 154(b) by 313 days.

(21) Appl. No.: 12/973,088

(22) Filed: Dec. 20, 2010

(65) Prior Publication Data

US 2012/0073582 A1 Mar. 29, 2012

(30) Foreign Application Priority Data

Sep. 24, 2010 (DE) .......................... 10 2010 046 369

(51) Int. Cl.
*A61F 5/56* (2006.01)
*A61C 5/14* (2006.01)
(52) U.S. Cl.
USPC .......................................... 128/848; 128/859
(58) Field of Classification Search
USPC ............ 128/848, 859–862; 433/6–7; 602/902
See application file for complete search history.

(56) References Cited

U.S. PATENT DOCUMENTS

| | | | | |
|---|---|---|---|---|
| 4,976,614 A | * | 12/1990 | Tepper | 433/18 |
| 6,109,265 A | * | 8/2000 | Frantz et al. | 128/848 |
| 6,983,752 B2 | * | 1/2006 | Garabadian | 128/848 |
| 7,178,529 B2 | * | 2/2007 | Kownacki | 128/848 |
| 2009/0032030 A1 | * | 2/2009 | Callender | 128/845 |
| 2010/0095970 A1 | | 4/2010 | Katz et al. | |

FOREIGN PATENT DOCUMENTS

| | | |
|---|---|---|
| DE | 295 06 512 U1 | 6/1995 |
| DE | 201 02 432 U1 | 4/2001 |
| DE | 20 2007 007 760 U1 | 9/2007 |
| DE | 202007007760 * | 10/2007 |
| DE | 10 2007 013 879 A1 | 9/2008 |
| WO | 2006/136684 A1 | 12/2006 |
| WO | 2008/023799 A1 | 2/2008 |

OTHER PUBLICATIONS

German Search Report for corresponding German Application No. 10 2010 046 369.8 dated Apr. 20, 2011.

* cited by examiner

*Primary Examiner* — Patricia Bianco
*Assistant Examiner* — Ophelia A Hawthorne
(74) *Attorney, Agent, or Firm* — Renner, Otto, Boisselle & Sklar, LLP

(57) ABSTRACT

An intraoral anti-snoring device, for shifting the lower jaw forward in relation to the upper jaw, with an upper jaw bar and a lower jaw bar that are both U-shaped and are connected to each other in a hinge joint at their outer flanks facing away from each other via protrusion ties by means of fixing buttons. At each of the two end sections of the protrusion tie, a round hole is provided for accepting the fixing button. The invention proposes a curved design for the protrusion tie, specifically an S-shaped design, with the center section having a cross-sectional contour—at least in part—that permits a temporary change of the distance of the round holes relative to each other by means of an elastic deformation of the protrusion tie in the longitudinal and in transverse direction. Preferably, the center section has an elongated hole that extends from one round hole to the other round hole and has a width that is smaller than or equal to the diameter of the round hole. Due to the resulting longitudinal edge strips that are capable of spring action, the fixing button is able to avoid excessive pressure by moving into the elongated hole.

7 Claims, 3 Drawing Sheets

ANTI-SNORING DEVICE

CROSS-REFERENCE TO RELATED APPLICATION

The present application claims priority under 35 USC §119 to German Patent Application No. 10 2010 046 369.8 filed Sep. 24, 2010, the entire disclosure of which is incorporated herein by reference.

TECHNICAL FIELD OF THE INVENTION

The invention relates to an anti-snoring device, for shifting the lower jaw forward in relation to the upper jaw, with an upper jaw bar and a lower jaw bar that are both U-shaped and are connected to each other in a hinge joint at their outer flanks facing away from each other via protrusion ties by means of fixing buttons. The upper and lower jar bar have receptacles for a first partial area of the fixing button and, at each of its two end sections, the protrusion tie has a round hole for accepting a second partial area of the fixing button, with the individual receptacles being staggered relative to each other in the extension direction of the upper jaw bar or the lower jaw bar.

DESCRIPTION OF THE RELATED ART

Snoring is usually caused by the weak muscle tone of the neck musculature during sleep. This leads to a narrowing of the respiratory passages or even to their closure. This automatically increases the flow of air and leads to a generation of noise due to the movement of the relaxed structures. With most people who snore, snoring occurs in dependence on the position of the body. Frequently, snoring is caused when the person is lying on the back, when the lower jar of the sleeper is not supported, moves backward and/or when the mouth is open.

Frequently, snoring persons do not enjoy a restful sleep because the snoring cycles occur above all during the important dream and deep-sleep phases. The results are exhaustion, nervousness, and fatigue when the person is awake, even if he/she slept for a long time. If they occur over the long term and are not diagnosed, more serious snoring disorders may lead to disorders of the cardiac and circulatory system (hypertension) with increased risks of cardiac infarction or strokes.

In addition, the snoring noise is usually very annoying for persons in the immediate surroundings of the snoring person. For the snoring person him/herself, snoring is even a health hazard, for example if an obstructive sleep apnea is present. In order to eliminate the negative social consequences of snoring and to avoid injury to the snoring person's health, a large number of devices, aids, face masks and even some surgical procedures are available that prevent snoring more or less effectively in many different ways.

Among others, anti-snoring devices for intraoral use have become known which, in case of mouth-breathing, shift the lower jaw forward relative to the upper jaw in order to achieve an opening of the pharyngeal portion of the respiratory passages. Along with the lower jaw, the base of the tongue is also moved forward, which makes the opening of the respiratory passages possible. Such devices are usually prescribed by dentists and are fitted by dentists to the jaw formation and to the dentition.

For example, an intraoral device for snoring therapy of the type referred to above is known from the design patent DE 295 06 512 U1. The design patent discloses an orally worn anti-snoring device consisting of an upper jaw bar and a lower jaw bar and a flexible connection of both bars which, however, cannot be extended in the longitudinal direction, and which, when the lower jaw drops during sleep, move the lower jaw automatically into an anterior position.

In this anti-snoring device, the upper jaw bar and the lower jaw bar each consists of a single-piece brace-type mouthpiece, and are fitted to the upper jaw and the lower jaw of the user and are contact-fitted to enclose the dentition. For example, the two bars consist of a cured plastic material, preferably PET, PMMA, or similar materials. However, the two bars may also consist of a combined soft and hard plastic layer. The ties (protrusion ties) are attached rotatably to the outsides of the upper jaw bar and the lower jaw bar by means of fixing buttons. By using protrusion ties of different lengths, the forward shift of the lower jaw can be easily adjusted to the needs of the individual user. On the upper jaw bar, the ties are attached in the region of the canines, and on the lower jaw bar in the region of the premolars. The protrusion tie consists of a flexible material such as nylon that does not stretch in the longitudinal direction.

The anti-snoring device referred to above has the disadvantage that wearing it is made significantly less comfortable due to a lack of give of the protrusion ties in the longitudinal direction that act as tension element when opening the mouth and as pressure element when closing the mouth. The movement of the lower jaw relative to the upper jaw is fixed by the length of the protrusion ties, and cannot be influenced at all by the user of the anti-snoring device during its application. Also, due to the fact that the protrusion ties neither stretch nor compress in the extension direction, there is a hard stop of the motion of the lower jaw when reaching the end position, which is also a disadvantage.

SUMMARY OF THE INVENTION

Starting with the prior art described above, the invention addresses the problem of proposing a solution where the intraoral anti-snoring device allows the user to influence the movement of the lower jaw to a limited extent.

The invention is based on the principal idea of making it possible for the user to exert a limited influence on the movement of the lower jar relative to the upper jar that is controlled by the anti-snoring device by providing, on both sides of the upper jaw bar and the lower jaw bar, one protrusion tie each that is stretchable and/or compressible in the extension direction for their connection in the form of a hinge. The length of change of the ties is reversible in that the protrusion ties are deformed elastically. This alters the distance of the round holes, located on the end sections, where the spring-action protrusion ties have a hinge connection with the upper jaw bar and the lower jaw bar by means of the fixing buttons. The elasticity of the protrusion tie can be influenced by selecting a suitable shape and a suitable material. Without any force acting on them, the two protrusion ties of the anti-snoring device are in a relaxed position.

In the intraoral anti-snoring device according to the invention, the center section of the protrusion tie connecting the end sections is curved, having a cross-sectional contour—at least in part—that permits a temporary change of the distance of the round holes relative to each other by means of an elastic deformation of the protrusion tie. For this purpose, the center section consists preferably of a spring element and is made from an elastic thermoplastic synthetic material.

In an advantageous embodiment of the invention, the center section of the protrusion tie has at least one elongated hole that is located between the round holes and extends substantially in the longitudinal direction of the protrusion tie while forming springy longitudinal edge strips. Advantageously, the elongated holes and the longitudinal edge strips have a curved shape like the outer contour of the protrusion tie, ideally matching each other. In principle, but being more costly to produce, the center section may comprise several elongated holes that are arranged one behind the other or side-by-side, and are separated from each other by at least one longitudinal or transverse center strip.

The form of the curve of the protrusion tie may be chosen at random, as long as it permits an elastic length change of the center section with a simultaneous width change of the center section. In terms of durability and user comfort of the anti-snoring device, an S-shaped contour proved to be ideal for the center section. In conjunction with an appropriately shaped elongated hole, this results in two S-shaped longitudinal edge strips capable of spring action.

The S-shape of the center section may continue into the end sections of the protrusion tie. A more complex variant, for example, may also have two S-shaped longitudinal edge strips and a longitudinal center strip of the same shape located in between, with all strips laterally bordering two S-shaped elongated holes extending side by side. Specifically, the S-shaped center section of the protrusion tie of the anti-snoring device according to the invention may have a single, double, or multiple S-shape.

Preferably, the center section in one embodiment of the invention has at least one elongated hole that is connected on its narrow side with at least one of the round holes of the protrusion tie. As a result, the fixing button connecting the upper jaw bar or the lower jaw bar with the protrusion tie can be moved from the round hole to the elongated hole and vice versa so that the distance between the two fixing buttons holding the protrusion tie can change. This makes it possible for the protrusion tie to act differently during the closing and the opening of the mouth, and that in the open as well as the closed position of the mouth the position of the lower jar relative to the upper jaw may be different, depending on the length of the elongated hole and the position of the fixing button, and may be influenced within these parameters by the user of the anti-snoring device according to the invention. When a certain pressure force is exerted on the protrusion tie, the fixing buttons unlock automatically from the round holes and slide into the elongated holes until an occurring tensile force moves the fixing buttons in the opposite direction towards the round holes, locking them there. For the user, this significantly increases the comfort of wearing the device.

The freedom of motion of the connecting fixing button can be determined by the width of the elongated hole relative to the diameter of the round hole. In a preferred embodiment of the anti-snoring device according to the invention, the width of the elongated hole is smaller than or equal to the diameter of the round hole. This results in a sliding seat for the fixing button that, in the first case, is impeded by the longitudinal edge strips and/or the longitudinal center strips that can be deflected transversely in their extension direction, but is unimpeded in the second case. Preferably, at the transition from the elongated hole to the round hole, a step or a narrow section is provided that has a snap effect during the movement of the fixing button from the round hole into the elongated hole and vice versa. The snapping of the fixing button out of or into the round hole can be felt by the user of the anti-snoring device and allows the user to influence the movement of the lower jaw to a limited degree.

The ability of the fixing button to move impeded or unimpeded from its basic position in the round hole to the alternate position in the elongated hole also helps to prevent damage to the protrusion tie caused by excessive axial pressure forces. In addition, it avoids the lateral deflection of the protrusion tie away from the upper jaw bar and the lower jaw bar in the direction of the user's cheek, thereby improving the user's feeling of comfort.

It proved to be favorable to make the fixing button a single piece. On the one hand, this facilitates the production and the installation of the button, while, on the other hand, ensures a good stability of the button, especially during its movement between the elongated and the round hole. Advantageously, from the inner flank in each case and through the preferably round receptacles of the upper jaw bars or the lower jaw bars, the fixing button can be locked, with minimal axial play and in a manner that makes it difficult to detach, into the round and/or the elongated hole of the protrusion tie whose end sections are in contact with the outer flanks of the bars.

To summarize briefly, compared with known devices, the new anti-snoring device according to the invention has the significant advantage of a distinctly improved comfort while in use and, in connection with that, a much higher acceptance that is due to the fact that the hinged connection of the upper and lower shell is engineered to be not completely rigid. Within a given framework, the distance of the points of engagement of the fixing buttons on the protrusion ties is variable and dependent on the force that acts on the protrusion tie in the longitudinal direction and can be influenced by the user him/herself. With a sufficient tensile force, the two protrusion ties are extended elastically, i.e. reversibly, in the longitudinal direction; in case of an excessive pressure force, the fixing buttons unlock from the round holes provided as support points and move into the elongated holes. This usually occurs when, relative to the upper jaw, the lower jaw reaches certain end positions determined by the anti-snoring device with the mouth closed or open. Due to the simple geometric shape of the protrusion tie and the single-piece design, it is, on the one hand, easier and therefore less expensive to manufacture the proposed anti-snoring device compared with known devices of this type and, on the other hand, it offers a much longer service life than these due to the damped stop of the lower jaw when reaching the end position.

Below, the invention is explained in detail with reference to an embodiment shown in the drawing. Additional characteristics of the invention are given in the following description of the embodiment of the invention in conjunction with the claims and the attached drawing. The individual characteristics of the invention may be realized either individually by themselves or in combinations of several in different embodiments of the invention.

DETAILED DESCRIPTION OF THE INVENTION

Figure 1:
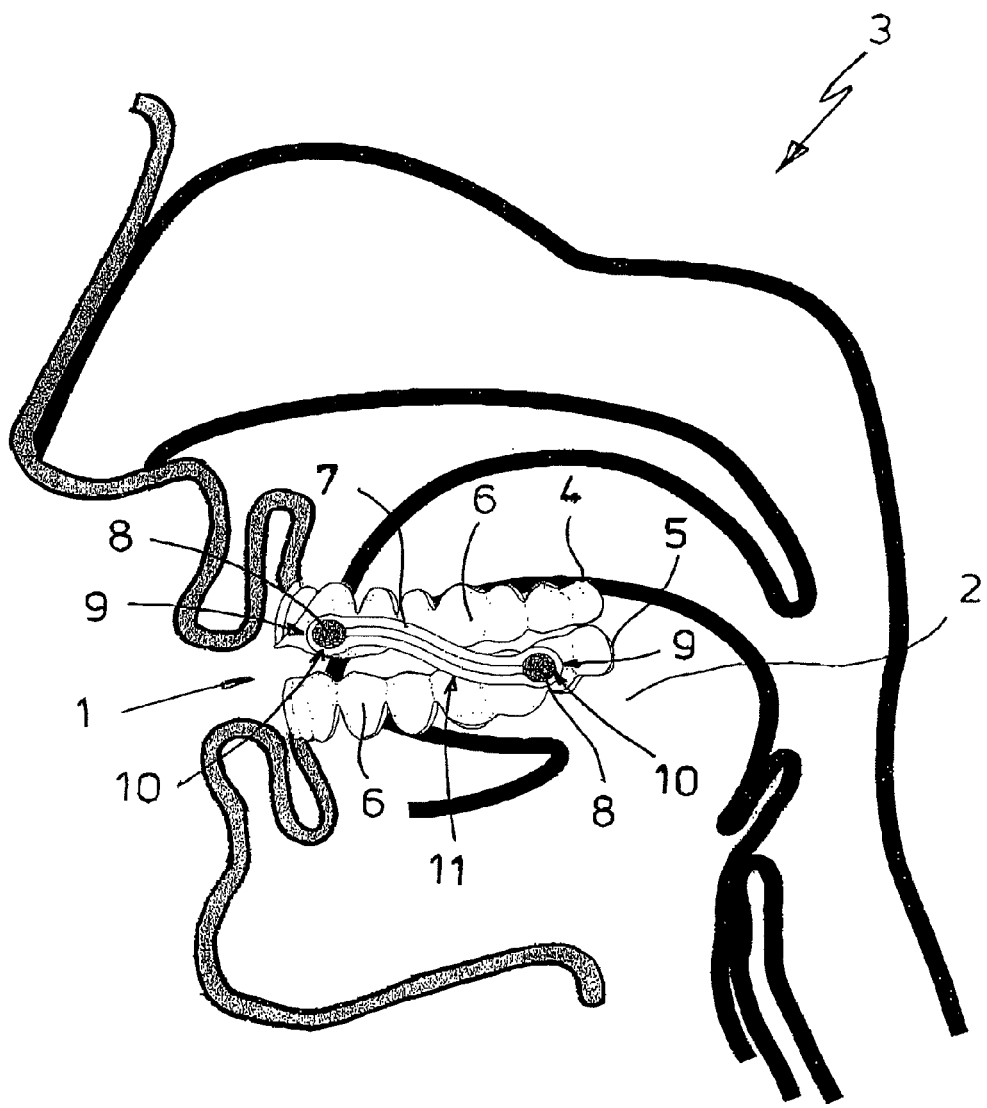
FIG. 1 shows a side view of the anti-snoring device according to the invention with an upper jaw bar and a lower jaw bar and the protrusion tie attached to the outside of the bars, inserted in the mouth of a user.

FIG. 1 shows an intraoral anti-snoring device 1 according to the invention for shifting the lower jaw forward relative to the upper jaw, inserted into the mouth 2 of a schematically represented head 3 of a user. The anti-snoring device 1 has an upper jaw bar 4 and a lower jaw bar 5 that are U-shaped and are connected to each other in a hinge joint at their outer flanks 6 facing away from each other via protrusion ties 7 by means of fixing buttons 8. The upper and lower jar bar 4, 5 has receptacles for a first partial area of the fixing button 8 that consists preferably of a single piece and, at each of its two end sections 9, the protrusion tie 7 has a round hole 10 for accepting a second partial area of the fixing button 8. The receptacles of the bars 4, 5 are staggered relative to each other in the extension direction of the upper jaw bar or the lower jaw bar 4, 5. In this embodiment, a center section 11 connecting the two end sections 9 is curved in an S-shape.

Figure 2:
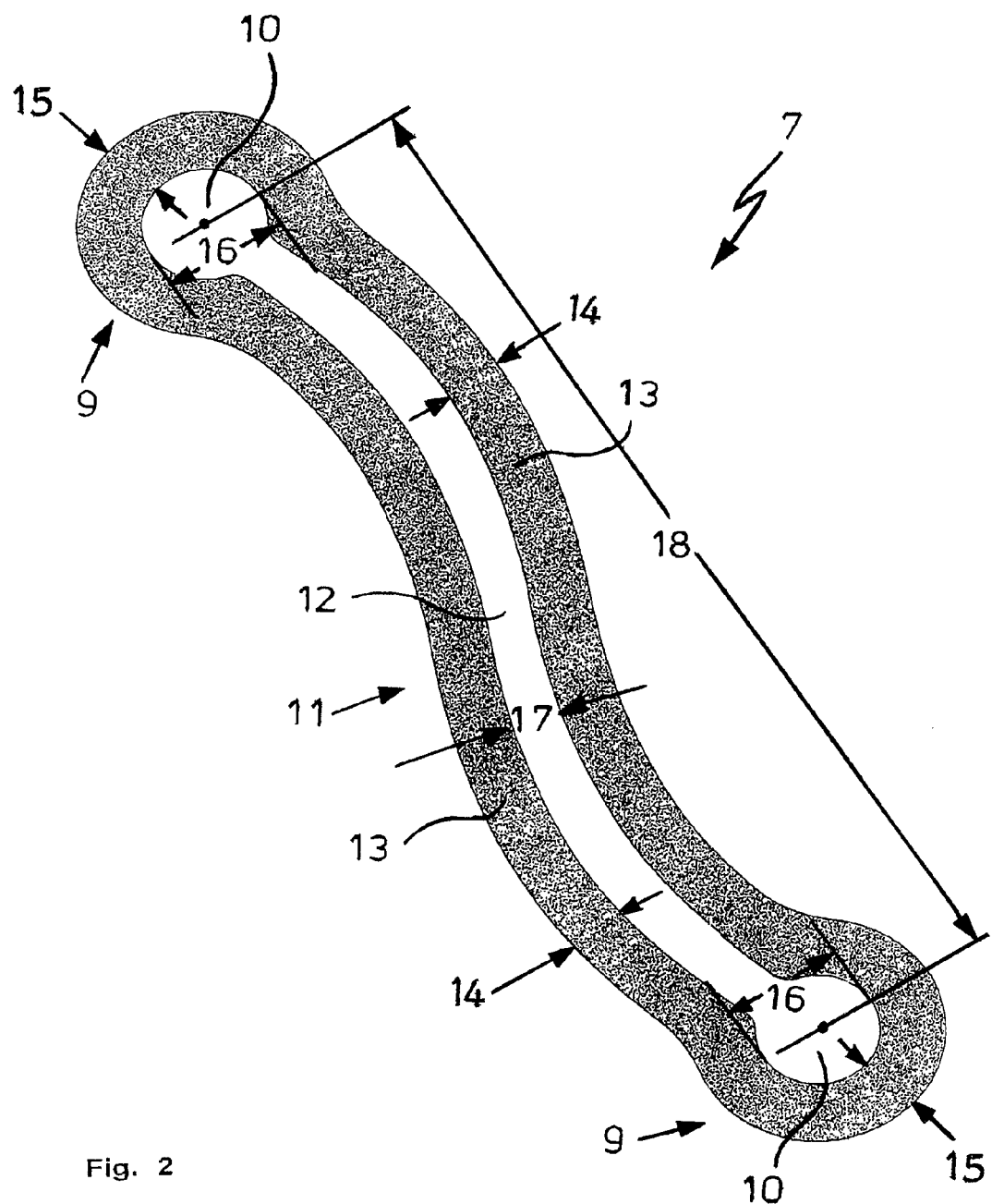
FIG. 2 shows a top view of the protrusion tie in FIG. 1 in an enlarged representation.

As the enlarged view of the protrusion tie 7 in FIG. 2 shows, the center section 11 has a cross-sectional contour—at least in part—that permits a temporary change of the distance of the round holes 10 relative to each other by means of an elastic longitudinal and transverse deformation of the protrusion tie 7. For this purpose, the protrusion tie 7 preferably has the typical geometry described below. The center section 11 has an elongated hole 12 that extends between the round holes 10. The elongated hole 12 is connected with the round holes 10 and defines two longitudinal edge strips 13 that extend on both sides of the elongated hole 12 from one to the other round hole 10. The longitudinal edge strips 13 and the elongated hole 12 have the advantageous S-shape of the outer contour of the center section 11 of the protrusion tie 7.

In this specific embodiment, a thickness of 1.0 mm was found to be especially suitable for the protrusion tie 7, preferably made of an elastic thermoplastic synthetic material, for example a nylon material, for achieving the desired spring characteristics of the protrusion tie 7 with a typical strip width 14 of the longitudinal edge strips 13 of approximately 1.3 mm in conjunction with a typical hole width 17 of the elongated hole 12. At the end sections 9 of the protrusion tie 7, the strip width 15 at the round holes 10 is typically approximately equal to the strip width 14 of the center section 11 on both sides of the elongated hole 12. Preferably, the diameter 16 of the round holes 10 corresponds to approximately twice the strip width 14 of the longitudinal edge strips 13.

FIG. 2 shows the protrusion tie 7 in relaxed position. For alternative embodiments of the anti-snoring device according to the invention, the tie 7 may have different overall lengths. This results in a different distance between the two round holes 10 so that the dentist making the anti-snoring device and fitting it to the jaw formation and the dental structure of the user can adjust the forward shift of the lower jaw individually by using protrusion ties 7 of different overall lengths. In the various embodiments of the tie 7, the distance 18 of the round holes 10 of the protrusion tie 7 is typically between 21.0 and 25.0 mm, in 1 mm increments, but other distances may also be chosen. This special construction has the effect that the protrusion tie 7 is very delicate and that, after precise fitting to the jaw formation of the user, the distance of the upper incisors from the lower ones amounts to only a few millimeters which has an extremely positive effect on user comfort and acceptance. The anti-snoring device 1 according to the invention is therefore also suitable for jaw formations of different sizes.

Figure 3:
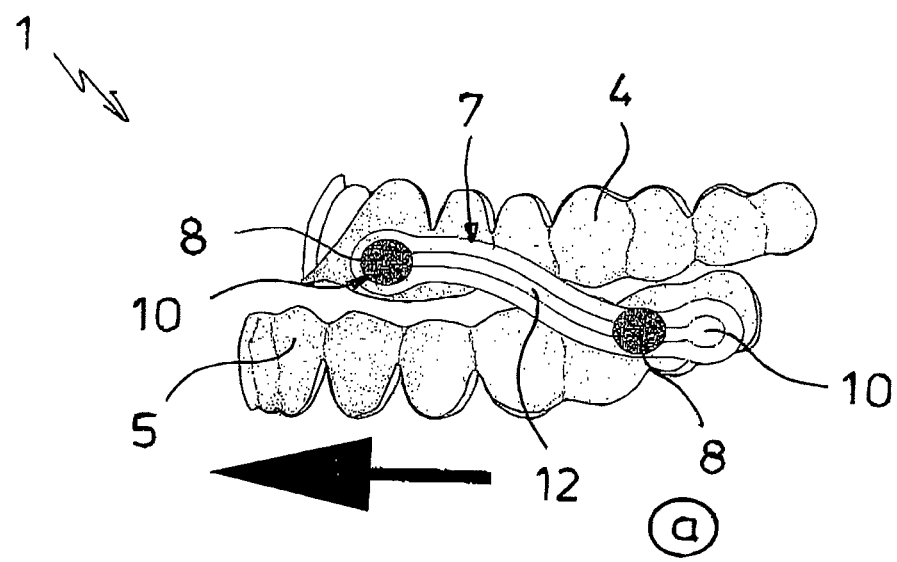
FIG. 3 shows the anti-snoring device according to FIG. 1 with the lower jaw bar shifted forward (FIG. 3a) and with the lower jaw bar shifted backward (FIG. 3b).
Figure 3:
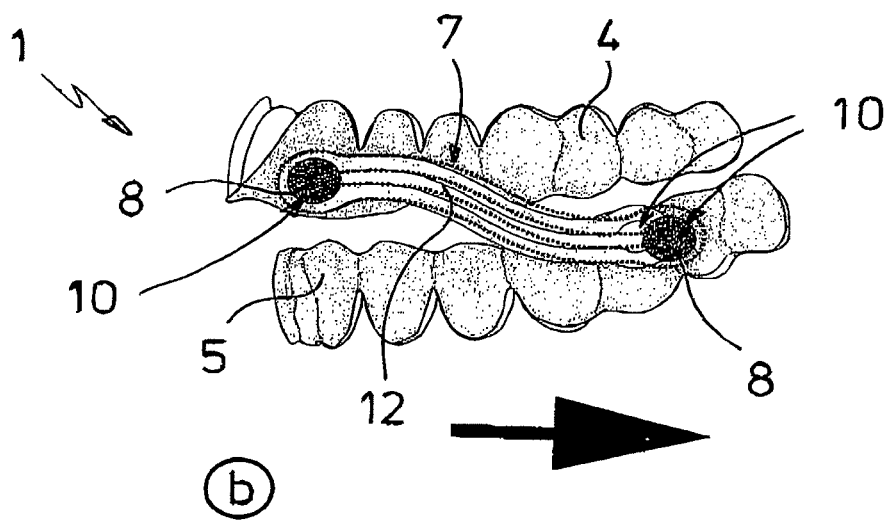

As described above, the elongated hole 12 with a preferred width of 1.2 mm is therefore distinctly smaller than the diameter 16 of the round holes 10 so that the springy longitudinal edge strips 13 impede the movement of the fixing button 8 from the round hole 10 to the elongated hole 12 by offering a certain resistance. This has the effect that, under a certain pressure force on the protrusion tie 7, the fixing button 8 noticeably unlocks from the round hole 10. When the direction of the motion is reversed, the fixing button 8 locks into the round hole 10 without resistance. FIG. 3b shows the lower jaw bar 5 shifted backward relative to the upper jaw bar 4, with the fixing buttons 8 held in the two round holes 10, i.e. in the normal position. The normal position of the protrusion tie 7 is shown by the solid lines, and the spring-like extended position of the tie 7 is shown by the dotted lines. By comparison, FIG. 3a shows the lower jaw bar 5 shifted forward relative to the upper jaw bar 4, as is the case when the mouth is open, with one of the fixing buttons 8 unlocked from the associated round hole 10 in the longitudinal direction of the protrusion tie 7, and positioned in the elongated hole 12.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

The invention claimed is:

1. An intraoral anti-snoring device, for shifting the lower jaw forward in relation to the upper jaw, with an upper jaw bar and a lower jaw bar that are both U-shaped and are connected to each other in a hinge joint at their outer flanks facing away from each other via protrusion brackets by means of fixing buttons, with each of the fixing buttons being rigidly fixed at the upper and lower jaw bar and being movably connected to the protrusion brackets that are stretchable and compressible and have a round hole at each end section of said protrusion brackets for accepting the fixing buttons being staggered relative to each other at the upper jaw bar and the lower jaw bar in the extension direction of said bars, wherein a center section of the protrusion brackets connecting the end sections is curved and is engineered as a spring element having a cross-sectional contour—at least in part—that permits a temporary change of a distance of the round holes relative to each other by elastically deforming the protrusion brackets, and wherein the center section has one elongated hole that is located between the round holes and extends substantially in the longitudinal direction over a large area of the center section of the protrusion brackets while forming longitudinal edge strips that are capable of spring action and wherein at least one of the narrow ends of the elongated hole is connected with one of the round holes of the protrusion brackets, so that the fixing buttons can be moved from the round hole to the elongated hole and vice versa, and wherein a step or a narrow section is provided at a transition from the elongated hole to the round hole that has a snap effect during the movement of the fixing button from the round hole into the elongated hole and vice versa.

2. The intraoral anti-snoring device according to claim 1, wherein the center section of the protrusion brackets consists of an elastic thermoplastic synthetic material.

3. The intraoral anti-snoring device of claim 2, wherein the elastic thermoplastic synthetic material is a nylon material.

4. The intraoral anti-snoring device according to claim 1, wherein a width of the elongated hole is smaller than or equal to a diameter of the round hole.

5. The intraoral anti-snoring device according to claim 1, wherein the protrusion brackets extend in an S-shaped curve in the longitudinal direction.

6. The intraoral anti-snoring device according to claim 1, wherein long sides of the elongated hole extend parallel to an outer contour of the center section.

7. The intraoral anti-snoring device according to claim 1, wherein the fixing buttons are made as a single piece.

* * * * *